United States Patent
Zanella et al.

(10) Patent No.: US 11,613,732 B2
(45) Date of Patent: Mar. 28, 2023

(54) CELL MEDIUM FORMULATION FOR CELL STABILIZATION

(71) Applicant: StemoniX Inc., Eden Prairie, MN (US)

(72) Inventors: Fabian Zanella, Eden Prairie, MN (US); Stephan Spangenberg, Eden Prairie, MN (US); Wonjong Si, Eden Prairie, MN (US); Ping Yeh, Eden Prairie, MN (US); Robert John Petcavich, The Woodlands, TX (US)

(73) Assignee: StemoniX Inc., Eden Prairie, MN (US)

( * ) Notice: Subject to any disclaimer, the term of this patent is extended or adjusted under 35 U.S.C. 154(b) by 1234 days.

(21) Appl. No.: 16/069,410

(22) PCT Filed: Jan. 12, 2017

(86) PCT No.: PCT/US2017/013192
§ 371 (c)(1),
(2) Date: Jul. 11, 2018

(87) PCT Pub. No.: WO2017/123759
PCT Pub. Date: Jul. 20, 2017

(65) Prior Publication Data
US 2019/0002831 A1   Jan. 3, 2019

Related U.S. Application Data

(60) Provisional application No. 62/277,870, filed on Jan. 12, 2016.

(51) Int. Cl.
*A01N 1/02* (2006.01)
*C12N 5/077* (2010.01)

(52) U.S. Cl.
CPC ........... *C12N 5/0657* (2013.01); *A01N 1/021* (2013.01); *A01N 1/0226* (2013.01); *C12N 2500/32* (2013.01); *C12N 2500/34* (2013.01); *C12N 2500/38* (2013.01); *C12N 2501/33* (2013.01); *C12N 2501/998* (2013.01)

(58) Field of Classification Search
CPC .............. C12N 5/0657; C12N 2500/32; C12N 2500/34; C12N 2500/38; C12N 2501/33; C12N 2501/998; A01N 1/021; A01N 1/0226
See application file for complete search history.

(56) References Cited

U.S. PATENT DOCUMENTS

| | | | | |
|---|---|---|---|---|
| 8,012,713 B2 * | 9/2011 | Chotani | ............... | C12N 9/2428 435/69.1 |
| 9,650,606 B2 * | 5/2017 | Hickman | ............. | C12N 5/0619 |
| 2005/0019922 A1 * | 1/2005 | Karube | ................. | C12N 13/00 435/446 |
| 2011/0312090 A1 | 12/2011 | Meyer et al. | | |

FOREIGN PATENT DOCUMENTS

| | | |
|---|---|---|
| JP | 2012508584 | 4/2012 |
| JP | 2013528401 | 7/2013 |
| JP | 2019501672 | 1/2019 |
| WO | WO-9738090 A1 | 10/1997 |
| WO | WO-2008112323 A1 | 9/2008 |
| WO | WO-2010039823 A2 | 4/2010 |
| WO | WO-2010057039 A2 | 5/2010 |
| WO | WO-2012037349 A2 | 3/2012 |
| WO | WO-2017123759 A1 | 7/2017 |

OTHER PUBLICATIONS

Francis, Geoffrey L. "Albumin and mammalian cell culture: implications for biotechnology applications." Cytotechnology. Jan. 2010; 62(1): 1-16. (Year: 2010).*
Arora, M. "Cell Culture Media: A Review." Mater Methods 2013;3:175 (Year: 2013).*
Zanella et al. "Patient-Specific Induced Pluripotent Stem Cell Models: Generation and Characterization of Cardiac Cells." Methods Mol Biol. 2016; 1353: 147-162. (Year: 2017).*
"Japanese Application Serial No. 2018-555832, Examiners Decision of Final Refusal dated Apr. 14, 2020", with English translation, 7 pages.
"European Application Serial No. 17701262.2, Communication Pursuant to Article 94(3) EPC dated Apr. 29, 2020", 9 pages.
"European Application Serial No. 17701262.2, Communication Pursuant to Article 94(3) EPC dated Jan. 15, 2021", 9 pages.
"European Application Serial No. 17701262.2, Response filed Mar. 18, 2019 to Communication Pursuant to Rule 161(1) and 162 EPC filed Oct. 24, 2018", 27 pgs.
"European Application Serial No. 17701262.2, Communication Pursuant to Article 94(3) EPC dated Jun. 28, 2019", 10 pages.
"Japanese Application Serial No. 2018-555832, Notification of Reasons for Refusal dated Jul. 9, 2019", (w English Translation), 15 pages.
"European Application Serial No. 17701262.2, Response filed Sep. 9, 2020 to Communication Pursuant to Article 94(3) EPC dated Apr. 29, 2020", 12 pages.
"Hibernate—A & Hibernate—E", Retrieved from the Internet: URL: <https://tools.thermofisher.com/content/sfs/manuals/Hibernate_A_E_PI.pdf>, (Jan. 1, 2014), 1-2 pgs.
"Hibernate E", Retrieved from the Internet: URL: <http://www.brainbitsllc.com/hibernate-e/>, (Jan. 1, 2017).
"International Application Serial No. PCT/US2017/013192, International Search Report dated Mar. 20, 2017", 7 pgs.
"International Application Serial No. PCT/US2017/013192, Written Opinion dated Mar. 20, 2017", 14 pgs.
"Medium 199 Components", Retrieved from the Internet: <https://www.thermofisher.com/de/de/home/technical-resources/media-formulation.86.html>, (Jan. 1, 2017), 1-3 pgs.
Abi-Gerges, Najah, et al., "Preservation of cardiomyocytes from the adult heart", Journal of Molecular and Cellular Cardiology, vol. 64, (Nov. 1, 2013), 108-119 pgs.
Anonymous, "B-27 Serum-Free Supplement (50X) liquid | Thermo Fisher Scientific", ThermoFischer Scientificc Website, Retrieved from the Internet: <https://www.thermofisher.com/nl/en/home/technical-resources/media-formulation.250.html>, (Jun. 13, 2016).

(Continued)

*Primary Examiner* — Titilayo Moloye

(74) *Attorney, Agent, or Firm* — Schwegman Lundberg & Woessner, P.A.

(57) ABSTRACT

A cell preservation medium, a cell recovery medium and a cell culture medium, and methods which employ the media, are provided.

5 Claims, No Drawings

(56) References Cited

OTHER PUBLICATIONS

Brewer, G J, et al., "Viable cultured neurons in ambient carbon dioxide and hibernation storage for a month", Retrieved from the Internet: URL: <http://www.ncbi.nlm.nih.gov/pubmed/8856709>, (Jun. 17, 1996), 1509-1512 pgs.

Heldt, S, "Coating plates & Primary Neuron Cell Cultures", Retrieved from the Internet:URL: <https://uthsc.edu/neuroscience/faculty/Heldt/pdfs/primary_cell_culture.pdf>, (Sep. 1, 2010), 1-3 pgs.

Liu, Y, et al., "Kruppel-like Factor 4 Abrogates Myocardin-induced Activation of Smooth Muscle Gene Expression", Journal of Biological Chemistry, vol. 280, No. 10, (Mar. 11, 2005), 9719-9727 pgs.

Louch, William, et al., "Methods in cardiomyocyte isolation, culture, and gene transfer", Journal of Molecular and Cellular Cardiology, Academic Press, GB, vol. 51, No. 3, (Jun. 6, 2011), 288-298 pgs.

"International Application Serial No. PCT US2017 013192, International Preliminary Report on Patentability dated Jul. 26, 2018", 13 pgs.

"European Application Serial No. 17701262.2, Response filed May 25, 2021 to Communication Pursuant to Article 94(3) EPC dated Jan. 15, 2021", 6 pages.

"Japanese Application Serial No. 2018-555832, Response filed Nov. 8, 2019 to Notification of Reasons for Refusal dated Jul. 9, 2019", with English claims, 6 pages.

"European Application Serial No. 17701262.2, Response filed Jan. 7, 2020 to Communication Pursuant to Article 94(3) EPC dated Jun. 28, 2019", 14 pages.

\* cited by examiner

CELL MEDIUM FORMULATION FOR CELL STABILIZATION

CROSS-REFERENCE TO RELATED APPLICATIONS

This application is a national stage application under 35 U.S.C. § 371 of PCT/US2017/013192, filed on Jan. 12, 2017, and published as WO 2017/123759 on Jul. 20, 2017, which claims the benefit of the filing date of U.S. application Ser. No. 62/277,870, filed on Jan. 12, 2016, the disclosures of which are incorporated by reference herein.

BACKGROUND

The long-term stabilization of cardiac muscle cells (cardiomyocytes) for transport is problematic due to poor survival of those cells under current cell preservation conditions. Traditionally, the preparation of cardiomyocytes for long-term transport involves cryopreservation of the cells in the form of a liquid suspension which: i) causes decreases in cell viability; ii) requires several manipulation steps to generate a cell suspension, and iii) requires that cells are stored and transported under cryogenic temperatures (−80 to −200° C.).

SUMMARY

The present disclosure provides, among other things, an aqueous medium formulation that allows cells, such as cardiomyocytes, to maintain cell viability and preserves cell function over periods of time of up to about 120 hours (5 days). Cells that are maintained in the conditions described herein have been successfully transported under standard courier handling and have been shown to retain full cell functionality and viability under non-cryogenic temperatures, e.g., temperatures from about 33° F. to about 75° F., for instance from about 35° F. to about 70° F. or from about 4° C. to about 30° C.

In one embodiment, the present disclosure provides an aqueous cell medium formulation comprising a cell hibernation medium that is supplemented with one or more reagents including reagents that support the stabilization of stem cell-derived progenitor or differentiated cells, such as stem-cell derived cardiomyocytes, for long-term transport. Also provided is a disclosure of compositions and reagents that enhance the recovery and restore the functionality of the cells after transport.

In one embodiment, the use of supplemented media formulations is provided, including formulations for cell transport (storage), for instance at room or ambient temperature, formulations for cell recovery and subsequent formulations for cell assays, including drug testing.

In one embodiment, the media formulations are employed with cells such as stem cells, for example, induced pluripotent stem cells, or cells differentiated from stem cells, such as stem cell-derived cardiomyocytes.

The formulations described herein, when used alone or in tandem (sequentially), have no or minimal impact on cell viability, e.g., relative to cells that are not subject to transport, allow cells, e.g., cardiomyocytes, to be preserved while attached to tissue culture vessels, overriding the need for obtaining a cell suspension, and/or provide for stabilization, storage and transport of cells, for instance, cardiomyocytes, at ambient temperatures (for example +15° C. to +25° C.).

For example, one formulation includes a cell preservation medium comprising a base medium, e.g., a cell hibernation medium, and L-glutamine or an analog thereof, and one or more, or any combination, of ascorbic acid, albumin, or insulin, in one embodiment, the cell hibernation medium comprises Hibernate®E. In one embodiment, the analog comprises L-alanyl-L-glutamine dipeptide. In one embodiment, the concentration of the L-glutamine or the analog dipeptide is about 0.5 mM to about 3 or 4 mM or about 1 mM to about 2 mM. In one embodiment, the ascorbic acid is about 100 µg/mL to about 300 µg/mL or about 150 to about 200 mM. In one embodiment, the albumin is about 200 µg/mL to about 700 µg/mL or about 300 to about 400 mM. In one embodiment, the insulin is about 1 µg/mL to about 20 µg/mL or about 4 µg/mL to about 6 µg/mL. In one embodiment, the medium comprises cells, e.g., cardiomyocytes.

A cell recovery medium is also provided. The cell recovery medium includes about 40% to about 60% of the cell preservation medium, about 10% to about 15% M199, about 35% to about 40% DMEM, glucose or other sugar based energy source, glutamine or an analog thereof, and one or more, or any combination, of ascorbic acid, albumin, and insulin. In one embodiment, the glucose or other sugar is about 2 g/L to about 8 g/L or about 4 g/L to about 5 g/L. In one embodiment, the L-glutamine or analog in the cell preservation medium or the cell recovery medium is about 0.5 mM to about 3 or 4 mM or about 1 mM to about 2 mM. In one embodiment, the ascorbic acid in the cell preservation medium or the cell recovery medium is about 100 µg/mL to about 300 µg/mL or about 150 µg/mL to about 200 µg/mL. In one embodiment, the albumin in the cell preservation medium or the cell storage medium is about 200 µg/mL to about 700 µg/mL or 300 µg/mL to 400 µg/mL. In one embodiment, the insulin in the cell preservation medium or the cell storage medium is about 1 µg/mL to about 20 µg/mL or 4 µg/mL to 6 µg/mL. In one embodiment, the medium comprises cells such as cardiomyocytes.

Further provided is a cell culture medium comprising M199, DMEM, L-glutamine or an analog thereof, glucose or other sugar based energy source, and one or more of ascorbic acid, albumin or insulin, in one embodiment, the cell culture medium comprises about 20% to about 30% M199, in one embodiment, the cell culture medium comprises about 70% to about 80% DMEM with L-glutamine. In one embodiment, the glucose or other sugar is about 2 g/L to about 8 g/L or about 4 g/L to about 5 g/L. In one embodiment, the concentration of the L-glutamine or the analog dipeptide is about 0.5 mM to about 3 or 4 mM or about 1 mM to about 2 mM. In one embodiment, the ascorbic acid in the cell culture medium is about 100 µg/mL to about 300 µg/mL or about 150 to about 200 mM. In one embodiment, the albumin in the cell culture medium is about 200 µg/mL to about 700 µg/mL or about 300 to about 400 mM. In one embodiment, the insulin in the cell culture medium is about 1 µg/mL to about 20 µg/mL or about 4 µg/mL to about 6 µg/mL. In one embodiment, the medium comprises cells, e.g., iPSc derived cardiomyocytes.

Methods of preparing cells for storage and shipment are provided, wherein the cells and the cell preservation medium are combined. After shipment, the cells are washed in the cell recovery medium and cultured in the cell culture medium.

This Summary is an overview of some of the teachings of the present application and not intended to be an exclusive or exhaustive treatment of the present subject matter. Further details about the present subject matter are found in the detailed description and appended claims

DETAILED DESCRIPTION

The following detailed description provides aspects and embodiments in which the present subject matter may be practiced. These embodiments are described in sufficient detail to enable those skilled in the art to practice the present subject matter. References to "an", "one", or "Various" embodiments in this disclosure are not necessarily to the same embodiment, and such references contemplate more than one embodiment. The embodiments of the following detailed description are demonstrative and not to be taken in a limiting sense.

In one embodiment, a preservation (stabilization) medium for cell transport includes cell hibernation medium (for instance, Hibernate®E) supplemented with biochemical entities that favor the survival and function of cells. For example, cardiomyocyte preservation medium includes cell hibernation medium (Hibernate®E) supplemented with reagents that enhance the survival and function of cardiomyocytes, e.g., L-glutamine or an analog thereof, e.g., L-alanyl-L-glutamine, ascorbic acid, albumin, for example, serum albumin such as human serum albumin, and/or insulin, for example, human insulin. Subsequently, when cells are to be recovered from stabilization after transport, media formulations that support the transition from a dormant, stable state to gradual metabolic and functional reactivation with minimal impact on cell viability, are employed.

The cells for transport may be in, for example, an individual vial or other container or in multi-well plates.

In one embodiment, to achieve cardiomyocyte preservation, cells are washed and placed in an appropriate volume of stabilization (preservation or hibernation) medium, in one embodiment, the stabilization medium includes Hibernate®E medium (Thermo Fisher Scientific Catalog number A12476), about 0.5 mM to about 4 mM L-glutamine or an analog thereof such as GlutaMax (Thermo Fisher Scientific Catalog number 35050), about 100 µg/mL to about 300 µg/mL ascorbic acid, about 200 µg/mL to about 700 µg/mL albumin, e.g., recombinant human serum albumin, and/or about 1 µg/mL to about 20 µg/mL insulin, e.g., recombinant human insulin, and optionally cells such as cardiomyocytes. In one embodiment, the stabilization medium includes Hibernate®E medium (Thermo Fisher Scientific Catalog number A12476), about 0.5 mM to about 3 mM, e.g., 0.75 mM to about 2.5 mM, L-glutamine or an analog thereof such as GlutaMax (Thermo Fisher Scientific Catalog number 35050), about 100 µg/mL to about 250 µg/mL, e.g., about 125 µg/mL to about 225 µg/mL, ascorbic acid, about 200 µg/mL to about 600 µg/mL, e.g., 250 µg/mL to about 450 µg/mL, albumin, e.g., recombinant human serum albumin, and/or about 1 µg/mL to about 15 µg/mL, e.g., about 3 µg/mL to about 7 µg/mL, insulin, e.g., recombinant human insulin, and optionally cells such as cardiomyocytes. In one embodiment, the stabilization medium includes Hibernate®E medium (Thermo Fisher Scientific Catalog number A12476), about 1.0 mM to about 3 mM L-glutamine or an analog thereof such as GlutaMax (Thermo Fisher Scientific Catalog number 35050), about 200 µg/mL to about 250 µg/mL ascorbic acid, about 400 µg/mL to about 600 µg/mL albumin, e.g., recombinant human serum albumin, and/or about 5 µg/mL to about 15 µg/mL insulin, e.g., recombinant human insulin, and optionally cells such as cardiomyocytes. Under these conditions and in the presence of appropriate gas exchange, cardiomyocytes can be maintained viable and their functionality is preserved for periods of time of at least two to at least five days. Other times are possible without departing from the scope of the present subject matter.

Following preservation, cells may be incubated for a period of time, for example, about 1 to about 24 hours, in a recovery solution containing about 30% to about 70% stabilization medium, e.g., about 50% stabilization medium as described above, and about 7% to about 20% M199 medium, e.g., about 12.5% M199 medium, about 25% to about 50% DMEM medium, e.g., about 37.5% DMEM medium, containing L-glutamine or an analog thereof, glucose or other energy source, ascorbic acid, albumin and/or insulin. In one embodiment, the recovery solution contains about 40% to about 60% stabilization medium, e.g., about 50% stabilization medium, as described above, about 7% to about 15% M199 medium, e.g., about 12.5% M199 medium, about 35% to about 45% DMEM medium, e.g., about 37.5% DMEM medium, containing L-glutamine or an analog thereof, such as about 2 mM to about 6 mM or about 3 mM to about 5 mM L-glutamine or an analog thereof, e.g., about 4 mM L-glutamine or an analog thereof, about 1.0 g/L to about 9 g/L or about 3.0 g/L to about 6.0 g/L glucose, for instance, about 4.5 g/L glucose, about 0.5 mM to about 4 mM L-glutamine or an analog thereof, about 100 µg/mL to about 300 µg/mL ascorbic acid, e.g., about 100 µg/mL to about 250 µg/mL ascorbic acid, about 200 µg/mL to about 700 µg/mL albumin, e.g., about 200 to about 600 µg/mL human serum albumin, about 0.1 µg/mL to about 20 µg/mL insulin, e.g., about 1 µg/mL to about 15 µg/mL human insulin, or any combination thereof, and optionally cells such as cardiomyocytes. In one embodiment, the recovery solution includes about 30% to about 70% stabilization medium, e.g., 50% stabilization medium, as described above, and about 7% to about 20% M199 medium, e.g., about 12.5% M199 medium, about 25% to about 50% DMEM medium, e.g., about 37.5% DMEM medium, containing L-glutamine or an analog thereof, glucose or other energy source, ascorbic acid, albumin and/or insulin, in one embodiment, the recovery solution contains about 40% to about 60% stabilization medium, e.g., about 50% stabilization medium, as described above, about 7% to about 15% M199 medium, e.g., about 12.5% M199 medium, about 35% to about 45% DMEM medium, e.g., about 37.5% DMEM medium, containing L-glutamine or an analog thereof, such as about 2 mM to about 6 mM or about 3 mM to about 5 mM L-glutamine or an analog thereof, g., about 4 mM L-glutamine or an analog thereof, about 1.0 g/L to about 9 g/L or about 3.0 g/L to about 6.0 g/L glucose, for instance, about 4.5 g/L glucose, about 100 µg/mL to about 250 µg/mL ascorbic acid, about 200 to about 600 µg/mL human serum albumin, about 0.1 µg/mL to about 2 µg/mL insulin, e.g., about 1 µg/mL to about 10 µg/mL human insulin, or any combination thereof, and optionally cells such as cardiomyocytes. Ceils may be placed in a 37° C., 5% $CO_2$ and 98% humidity incubator and allowed to recover for about 1 to about 48 hours, e.g., about 18 to about 24 hours, after which functionality may be re-gained. Functionality for cardiomyocytes may be detectable through spontaneous beating behavior.

Following recovery, and in preparation for the use of cells for physiological assays, cells may be placed in medium containing about 10% to about 40% M199 medium, e.g., about 254% M199 medium, about 60% to about 90% DMEM medium, e.g., about 75% DMEM medium, containing L-glutamine or an analog thereof, glucose or other energy source, ascorbic acid, albumin and/or insulin, in one embodiment, the recovery medium includes about 20% to about 30% M199 medium, e.g., about 25% M199 medium, about 65% to about 85% DMEM medium, e.g., about 75% DMEM medium, containing L-glutamine or an analog thereof, about 0.5 mM to about 4 mM, about 3.0 g/L to about 6.0 g/L glucose, for instance, about 4.5 g/L glucose, about 100 µg/mL to about 300 µg/mL ascorbic acid, e.g., about 100 µg/mL to about 250 µg/mL ascorbic acid, about 200 µg/mL to about 700 µg/mL albumin, e.g., about 200 µg/mL to about 600 µg/mL albumin, and/or about 0.1 µg/mL to about 20 µg/mL insulin, e.g., about 1 µg/mL to about 15 µg/mL human insulin, and optionally cells such as cardiomyocytes. In one embodiment, the recovery medium includes about 20% to about 30% M199 medium, e.g., about 25% M199 medium, about 65% to about 85% DMEM medium, e.g., about 75% DMEM medium, containing L-glutamine or an analog thereof, about 0.5 mM to about 4 mM, about 4.0 g/L to about 5.0 g/L glucose, for instance, about 4.5 g/L glucose, about 200 µg/mL to about 300 µg/mL ascorbic acid, e.g., about 200 µg/mL to about 250 µg/mL ascorbic acid, about 200 µg/mL to about 700 µg/mL albumin, e.g., about 450 µg/mL to about 550 µg/mL albumin, and/or about 0.1 µg/mL to about 20 µg/mL insulin, e.g., about 5 µg/mL to about 15 µg/mL human insulin, and optionally cells such as cardiomyocytes. Cells are maintained in a 37° C., 5% $CO_2$ and 98% humidity incubator for additional time, e.g., about 24 to about 48 hours, after which they can be used in a wide variety of cell-based assays.

For example, a cell preservation medium may include a cell hibernation medium such as Hibernate®E, a concentration of L-glutamine or an analog dipeptide thereof at about 0.5 mM to about 4 mM or about 1 mM to about 2 mM, a concentration of ascorbic acid at about 100 µg/mL to about 300 µg/mL or about 150 to about 200 mM, a concentration of albumin at about 200 µg/mL to about 700 µg/mL or about 300 to about 400 mM and a concentration of insulin at about 1 µg/mL to about 20 µg/mL or about 4 to about 6 mM. Cells such as cardiomyocytes, e.g., iPSc derived cardiomyocyte, are combined with the preservation medium. After transport, the cells are combined with a cell recovery medium. For instance, a cell recovery medium includes the cell preservation medium, M199, DMEM, glucose or other sugar based energy source, glutamine or an analog thereof, and one or more of ascorbic acid, albumin, or insulin, wherein the cell recovery medium has about 45% to about 55% cell preservation medium, wherein the cell recovery medium has about 10% to about 15% M199 and about 35% to about 40% DMEM. The cell recovery medium may include a concentration of glucose of about 2 g/L to about 8 g/L or about 4 g/L to about 5 g/L glucose or other sugar, a concentration of L-glutamine or analog of about 0.5 mM to about 4 mM or about 1 mM to about 2 mM, a concentration of ascorbic acid of about 100 µg/mL to about 300 µg/mL or about 150 µg/mL to about 200 µg/mL, a concentration of albumin of about 200 µg/mL to about 700 µg/mL or 300 µg/mL to about 400 µg/mL, and a concentration of insulin of about 1 µg/mL to about 20 µg/mL or 4 µg/mL to about 6 µg/mL. Subsequently the cells are culture in a cell culture medium. The cell culture medium includes M199, DMEM, L-glutamine or an analog thereof, glucose or other sugar based energy source, and one or more of ascorbic acid, albumin or insulin, wherein the medium comprises about 20% to about 30% M199, about 70% to about 80% DMEM, and about 2 g/L to about 8 g/L glucose or other sugar. The concentration of glucose or other sugar in the cell culture media is about 4 g/L to about 5 g/L, the concentration of ascorbic acid is about 100 µg/mL to about 300 µg/mL, the concentration of the albumin is about 200 µg/mL to about 700 µg/mL, the concentration of insulin is about µg/mL to about 20 µg/mL, and the concentration of L-glutamine or analog thereof is about 0.5 mM to about 4 mM.

The following is a non-limiting example of the compositions and methods.

EXAMPLE iPSc derived cardiomyocytes were loaded into a 384 well microplate and were placed in the preservation medium (hibernation medium) medium having about 2 mM Glutamax, about 215 µg/mL ascorbic acid, about 500 µg/mL human serum albumin, and about 10 µg/mL human insulin. The plate was sealed with a lid that allowed both oxygen and carbon dioxide gas exchange. The plate was then packaged into protective foam lined shipping envelope and subsequently into a FedEx shipping box. The plate and hibernating cells where then shipped from San Diego, California to Houston Texas using 3 day service. Upon arrival, the shipping container was inspected for damage and immediately shipped back to San Diego via overnight delivery. The total duration of the shipping test was 4 days. Upon arrival, the plate was removed, the lidding was peeled off, and the media in the microplate wells were exchanged with standard growth media. The cardiomyocytes started beating within 1 hour after media exchange, which validated the system.

Exemplary Embodiments

In one embodiment, a cell preservation medium is provided that comprises: cell hibernation medium and L-glutamine or an analog thereof, and one or more of ascorbic acid, albumin, or insulin. In one embodiment, the cell preservation medium comprises Hibernate®E (include calcium, magnesium, sodium phosphate, sodium bicarbonate, and sodium pyruvate, but is serum-free, glutamic acid-free, glutamine-free, antibiotic-free, and HEPES-free). In one embodiment, the analog comprises L-alanyl-L-glutamine dipeptide. In one embodiment, the concentration of the L-glutamine or the analog dipeptide is about 0.5 mM to about 4 mM. In one embodiment, the ascorbic acid is about 100 µg/mL to about 300 µg/mL. In one embodiment, the albumin is about 200 µg/mL to about 700 µg/mL. In one embodiment, the insulin is about 1 µg/mL to about 20 µg/mL. In one embodiment, the cell preservation medium comprises Hibernate®E, 2 mM Glutamax, 213 µM ascorbic acid, 500 µM recombinant human serum albumin, and 10 µM recombinant human insulin.

Also provided is a cell recovery medium comprising the cell storage medium, and M199 (includes Earle's salts), DMEM, glucose or other sugar based energy source, glutamine or an analog thereof, and one or more of ascorbic acid, albumin, and insulin. In one embodiment, the L-glutamine or analog in the cell storage medium is about 0.5 mM to about 4 mM. In one embodiment, the ascorbic acid in the cell storage medium is about 100 µg/mL to about 300 µg/mL. In one embodiment, the albumin in the cell storage medium is about 200 µg/mL to about 700 µg/mL. In one embodiment, the insulin in the cell storage medium is about 1 µg/mL to about 20 µg/mL. In one embodiment, the cell recovery medium comprises 50% cell preservation media having Hibernate®E 2 mM Glutamax, 213 µM ascorbic acid, 500 µM recombinant human serum albumin, and 10 µM recombinant human insulin, 12.5% M199, 37.5% DMEM with L-glutamine (4 mM), 4.5 g/L glucose, 213 µM ascorbic acid, 500 μM recombinant human serum albumin, and 10 μM recombinant human insulin.

Further provided is a cell culture medium comprising: M199, DMEM, L-glutamine or an analog thereof, glucose or other sugar based energy source, and one or more of ascorbic acid, albumin or insulin, in one embodiment, the ascorbic acid in the cell storage medium is about 100 μg/mL to about 300 μg/mL. In one embodiment, the albumin in the cell storage medium is about 200 μg/mL to about 700 μg/mL, in one embodiment, the insulin in the cell storage medium is about 1 μg/mL to about 20 μg/mL. In one embodiment, the L-glutamine or analog in the cell storage medium is about 0.5 mM to about 4 mM. In one embodiment, the cell culture medium comprises 25% M199, 75% DMEM with L-glutamine (4 mM), 4.5 g/L glucose, 213 μM ascorbic acid, 500 μM recombinant human serum albumin, and 10 μM recombinant human insulin.

The subject matter herein is described by example and different ways of practicing the subject matter have been described. However the subject matter covered by this application is not limited to any one specific embodiment or use or their equivalents. While particular embodiments of the method for fabricating cell micro arrays with subsequent drug dosing have been described it will be appreciated by those skilled in the art that changes and modifications may be made thereto without departing from the invention and as set forth in the following claims.

What is claimed is:

1. A cell recovery medium comprising:
M199, DMEM, glucose or other sugar based energy source, and cell preservation medium, wherein the cell recovery medium has about 45% to about 55% cell preservation medium, wherein the cell recovery medium has about 10% to about 15% M199 and about 35% to about 40% DMEM, wherein the cell preservation medium comprises cell hibernation medium, 0.5 mM to 4 mM L-glutamine or-alanyl-L-glutamine dipeptide, ascorbic acid, albumin, and insulin, wherein the ascorbic acid is 100 μg/mL to 300 μg/mL, the albumin is 200 μg/mL to 700 μg/mL, and the insulin is 1 μg/mL to 20 μg/mL.

2. The medium of claim 1, which comprises about 2 g/L to about 8 g/L or about 4 g/L to about 5 g/L glucose or other sugar.

3. The medium of claim 1, wherein the L-glutamine or alanyl-L-glutamine dipeptide in the cell recovery medium is about 1 mM to about 2 mM, the ascorbic acid in the cell recovery medium is about 150 μg/mL to about 200 μg/mL, the albumin in the cell recovery medium is about 300 μg/mL to 400 μg/mL, and the insulin in the cell recovery medium isabout 4 μg/mL to 6 μg/mL.

4. The cell recovery medium of claim 1 further comprising cells, thereby providing a mixture.

5. The medium of claim 4 wherein the cells are cardiomyocytes.

* * * * *